US009857300B2

(12) United States Patent
Pruneri et al.

(10) Patent No.: US 9,857,300 B2
(45) Date of Patent: Jan. 2, 2018

(54) APPARATUS FOR MEASURING LIGHT SCATTERING

(71) Applicants: Valerio Pruneri, Castelldefels (ES); Pedro Antonio Martínez Cordero, Castelldefels (ES); Marc Jofre Cruanyes, Castelldefels (ES)

(72) Inventors: Valerio Pruneri, Castelldefels (ES); Pedro Antonio Martínez Cordero, Castelldefels (ES); Marc Jofre Cruanyes, Castelldefels (ES)

(73) Assignee: Fundacio Institute De Ciencies Fotoniques, Barcelona (ES)

( * ) Notice: Subject to any disclaimer, the term of this patent is extended or adjusted under 35 U.S.C. 154(b) by 386 days.

(21) Appl. No.: 14/616,062

(22) Filed: Feb. 6, 2015

(65) Prior Publication Data

US 2015/0219555 A1 Aug. 6, 2015

(30) Foreign Application Priority Data

Feb. 6, 2014 (EP) .................................. 41382043

(51) Int. Cl.
  *G01N 21/47* (2006.01)
  *G01N 21/84* (2006.01)
  *G01N 21/57* (2006.01)

(52) U.S. Cl.
  CPC ............. *G01N 21/47* (2013.01); *G01N 21/57* (2013.01); *G01N 2201/0407* (2013.01)

(58) Field of Classification Search
  CPC .... G01N 21/57; G01N 21/47; G01N 21/8422; G01N 2201/0407; G01N 2201/12; G01N 2201/062
  See application file for complete search history.

(56) References Cited

U.S. PATENT DOCUMENTS

| 4,160,914 A | 7/1979 | Wynn |
| 5,093,837 A | 3/1992 | Edwards |

(Continued)

FOREIGN PATENT DOCUMENTS

DE  41 37 141 A1  6/1992

OTHER PUBLICATIONS

Notification of Transmittal of the European Search Report of the International Searching Authority dated Jul. 4, 2014 in connection with European Application No. 14 38 2043.

(Continued)

*Primary Examiner* — Evan Pert
*Assistant Examiner* — Changhyun Yi
(74) *Attorney, Agent, or Firm* — Gary J. Gershik; Cooper & Dunham LLP

(57) ABSTRACT

Apparatus for measuring light scattering of a sample comprising a light beam source, means for collimating the beam and making it impinge on the sample in a perpendicular direction, at least one light sensor, and at least one spatial filter between the sample and the optical sensor, provided with two apertures, means for measuring the total power reaching the sensor and means for measuring the power of beams with a low k vector after the beam traverses the filter. The invention provides thus a simplified, portable and compact device for measuring different parameters like haze, turbidity, etc. can be built, for any sample and without the need of changing detectors.

16 Claims, 14 Drawing Sheets

(56) References Cited

U.S. PATENT DOCUMENTS

2003/0118223 A1* 6/2003 Rahn .................... G01N 23/046
                                                            382/131
2010/0226524 A1   9/2010 Shakespeare et al.
2010/0277734 A1* 11/2010 Weichselbaum ....... G01N 21/51
                                                            356/338

OTHER PUBLICATIONS

European Office Action of the European Patent Office dated Jun. 24, 2016 in connection with European Application No. 14 382 043.9.

* cited by examiner

APPARATUS FOR MEASURING LIGHT SCATTERING

RELATED APPLICATIONS

This application claims priority of European Patent Application No. 41 382 043.9, filed Feb. 6, 2014, the entire contents of which are hereby incorporated by reference into this application.

BACKGROUND OF THE INVENTION

Field of the Invention

The present invention relates to an apparatus for measuring light scattering, haze and other related properties produced by non uniform liquid, solid or gas samples, both in their bulk or surface state.

Description of the Related Art

Light that is scattered upon passing through a film or sheet of a material can produce a hazy or smoky field when objects are viewed through the material. Another effect can be veiling glare, as occurs in an automobile windshield when driving facing the sun. Turbidity is a monitoring parameter used in various fields, such as food industry, water contamination control and water purification plants. Turbidimeters are used, for instance, in wine and beer production, in order to measure the total suspended solids value in a liquid sample. Very often, an inspection image is also needed in order to identify different suspended solids in the sample and their concentrations. Another example could be cheese production in which milk coagulation scattering and clustering effects are off-line monitored.

Haze, glare and gloss are scattering-related monitoring parameters also used in roll-to-roll plastic sheet, glass or film production. These parameters are usually measured off-line with different devices, of high cost and large dimensions, in order to detect imperfections and inhomogeneities in the samples. After the imperfection is detected, an image usually follows to determine its nature. It is desirable to measure such image using the same apparatus that is used to evaluate the scattering.

Haze in a film results in a cloudy appearance or poorer clarity of objects when viewed through the film. This is why haze is a parameter that characterizes transparent and translucent films, not opaque films A Hazemeter measures the haze (light forward scattering) and the light transmitting properties of plastic sheets, film, glass, and liquid products. They are used in many industry fields such as adhesives, Automotive, Ceramics, Chemical, Coatings, Cosmetics, Detergents, Dyestuffs, Food, Glazing products, Printing Inks, Packaging materials, Petroleum, Pharmaceuticals, Plastics, Polishes, Resins, Varnish, Waxes, etc. . . . . American Society for Testing and Materials (ASTM) standards establish that haze is the ratio of the light scattered at an angle larger than 2.5 degree and the total light exiting the sample at any angle.

Haze measurement is regulated by the standard ASTM D 1003 "Standard Test Methods for Haze and Luminous Transmittance of Transparent Plastics" and ASTM E 167/ ASTM E2387 for haze greater than 30%.

The ASTM procedure to measure haze consists on an easy calculation from four measurements:

$$H[\%] = 100 * \left( \frac{P_{HA}^S}{P_T^S} - \frac{P_{HA}^R}{P_T^R} \right) \quad (1)$$

$P_{HA}^S$ is the light power corresponding to beams with angles equal or greater than 2.5° emerging from sample. (HA: High Angles)

$P_{HA}^R$ is the light power corresponding to beams with angles greater than 2.5° emerging from sample holder plane but without any sample placed in.

$P_T^S$ is the total light power emerging from sample.

$P_T^R$ is the total light power emerging from sample holder plane but without any sample placed in.

A light k vector is defined as a magnitude and direction of a light beam: Its magnitude is either the wavenumber or angular wavenumber of the wave (inversely proportional to the wavelength), and its direction is ordinarily the direction of wave propagation.

High k vectors are defined as vectors whose direction forms an angle equal or greater than 2.5° with respect to the direction perpendicular to the sample surface under test. Low k vectors are defined as those whose direction forms an angle lower than 2.50.

The standard haze measurement aims to obtain the power ratio between the high k and the total k vectors emerging from the sample. A final correction with the haze reference is mandatory to reduce, if not eliminate, systematic errors.

Every commercial hazemeter that, according to ASTM standards, carries out two separate measurements, of the high k and total k vectors, requires blocking or rejecting the low k vectors. This comes always with an issue: there is a minimum distance between the sample and optical detector element that should exist in order to avoid geometrical errors. This is represented in FIG. 1a. When the distance between the sample and the low k light blocking or rejecting stage is too short (d1), too many high k vectors are blocked (besides the low k vectors). At increasing distances this effect is reduced, e.g. d2 is lower than for d1. In order that this effect is negligible, one has to reach a minimum distance (d3), which depends on the beam size (D). Note that also the blocking stage has to be increased in diameter with the distance because of intrinsic diffraction effects. Note that d3 also sets the resolution of this scheme. The smaller the distance the larger the contribution from k vectors further from 2.5 degree angle. In other words, the larger d3 is, the clearer the separation between k vectors. This is a important drawback because, correspondingly, the device requires a minimum size, sometimes this becoming an unpractical feature, especially for in-line measurements. Commercial hazemeters usually use an integration sphere (see FIG. 1b), which is an optical device that concentrates all the k vectors to one point inside it, with an on/off window. The collimated light source and an integrating sphere must be placed on opposite sides of the sample and must be structurally interconnected in order to preserve the alignment between source and integrating sphere. When the window is open, low k vectors escape from the integration sphere and an optical sensor inside the integration sphere measures only the high k vectors. When the window is closed, the optical sensor measures the total k vectors. In FIG. 1b, distance d3 has been defined as the minimum distance between the sample and the blocking stage in order to separate high from low k vectors. For a hazemeter according to the state of the art, with a beam diameter of 2.5 cm, the minimum d needed applying ASTM D1003 (that is, the needed Integration Sphere diameter) is 28.63 cm. This distance limits the size and configuration of the device.

An alternative way of calculating the haze of a sample is described in WO2010/104699. The method comprises measuring the power of high k vectors and adding it to that of low k-vectors. This method however has the drawback that rays with a k-vector greater than the radius of the sensor will not be detected. The detector must be thus adapted to the dimensions of the sample. A sensor is expensive and thus, having a set of them for different samples results costly.

There is thus a need for a method and device for measuring light scattering with smaller size, lower cost components, making it also possible to be used for in-line measurements.

SUMMARY OF THE INVENTION

The invention, in its simplest form, includes a light source, a sample holder, at least one light sensor and at least one spatial filter, each filter having two apertures of equal or different diameters for removing the scattered light beams above a predefined angle, that we name cut-off angle. In other embodiments, an array of spatial filters having different cut-off angles can be used. In this case, multiple photodetectors or an array of photodetectors, such as complementary metal-oxide-semiconductor (CMOS) or charge-coupled device (CCD) light sensor, are preferred. In other cases, one or two photo diodes might be sufficient. In some cases the sample holder may not be needed, as it is for example for in-line measurements of thin film sheets. The filter can be continuous, with two apertures, or be constituted by two separate apertures, which must meet the following relation:

$$\alpha_c = \arctan\left(\frac{D_1 + D_2}{2 \cdot L}\right)$$

wherein $\alpha_c$ is the scattering angle, D1 an D2 the diameters of the apertures and L the total length of the filter in the direction of the beam. The combination of at least one spatial filter with an light sensor offers the possibility to obtain at the same time a microscopic image of the illuminated area (within the sensor area) as well as values of the light scattering, i.e. a haze value at predefined cut-off angles if the measurement is in transmission from a gel or solid sample, a gloss value if the measurement is in reflection from a gel or solid sample, or a turbidity value if the measurement is in transmission from a liquid sample. The device can also be used as a turbidimeter if the sample is a liquid one. Other advantageous embodiments are defined in the dependent claims.

BRIEF DESCRIPTION OF THE DRAWINGS

To complete the description and in order to provide for a better understanding of the invention, a set of drawings is provided. Said drawings illustrate a preferred embodiment of the invention, which should not be interpreted as restricting the scope of the invention, but just as an example of how the invention can be embodied.

DETAILED DESCRIPTION OF THE INVENTION

The invention filters and measures the optical power of a representative part of low k vectors (defined as low k power) and a representative part of the total k vectors (defined as a total k power) power by means of at least one filter with two apertures. The light source can be of any predetermined wavelength or white, tunable or it can be a light emitting diode. In this way a simplified, portable and compact device for measuring different parameters like haze, turbidity, etc. can be built, for any sample and without the need of changing detectors.

Indicating with $P_{LA}$ the light power corresponding to beams (k vectors) with angles lower than 2.5°, $P_{HA}$ the light power corresponding to beams (k vectors) with angles equal or greater than 2.5°, and $P_T$ the total light power emerging from sample:

$$P_T = P_{LA} + P_{HA} \tag{2}$$

And consequently:

$$P_{HA} = P_T - P_{LA} \tag{3}$$

The haze expression (1) as a function of low and total k vectors powers:

$$H[\%] = 100 * \left[\left(1 - \frac{P_{LA}^S}{P_T^S}\right) - \left(1 - \frac{P_{LA}^R}{P_T^R}\right)\right] \tag{4}$$

$$H_S = \left(1 - \frac{P_{LA}^S}{P_T^S}\right)$$

is the haze from the sample and $$H_R = \left(1 - \frac{P_{LA}^R}{P_T^R}\right)$$

is the reference haze (measurement without sample).

Figure 1A:
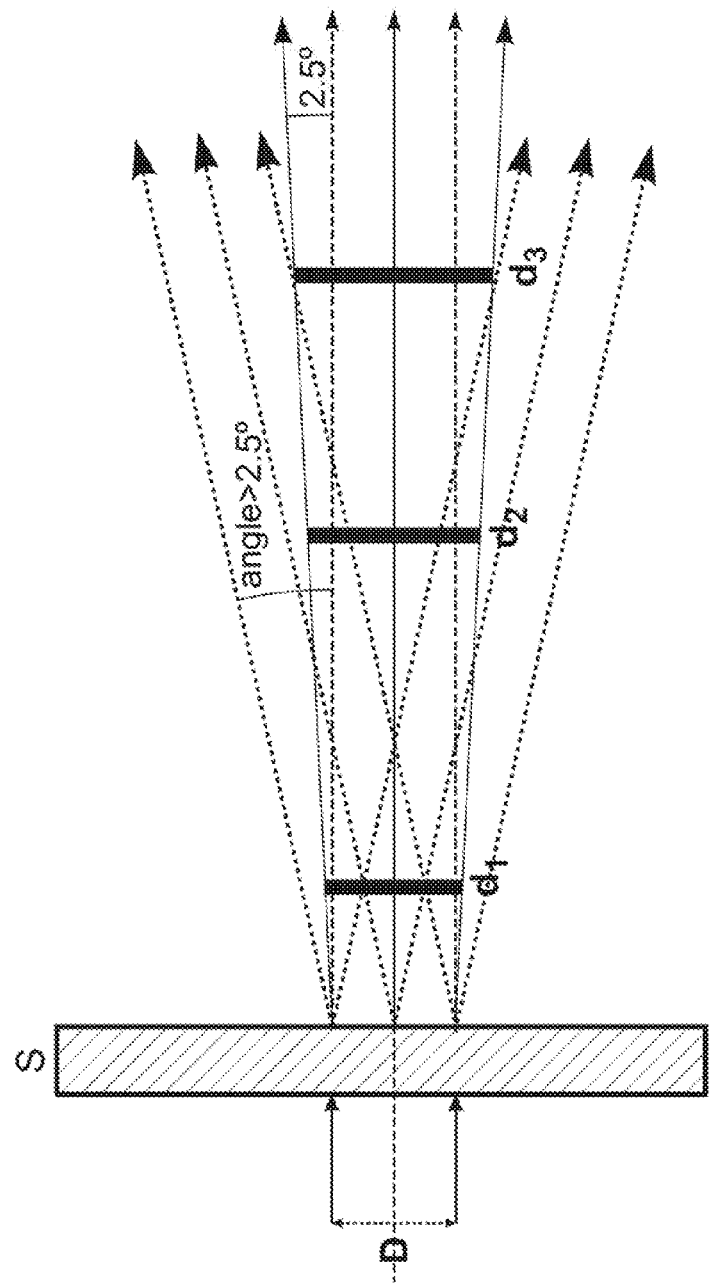
FIGS. 1a and 1b show the technical problem related with the prior art.
Figure 1B:
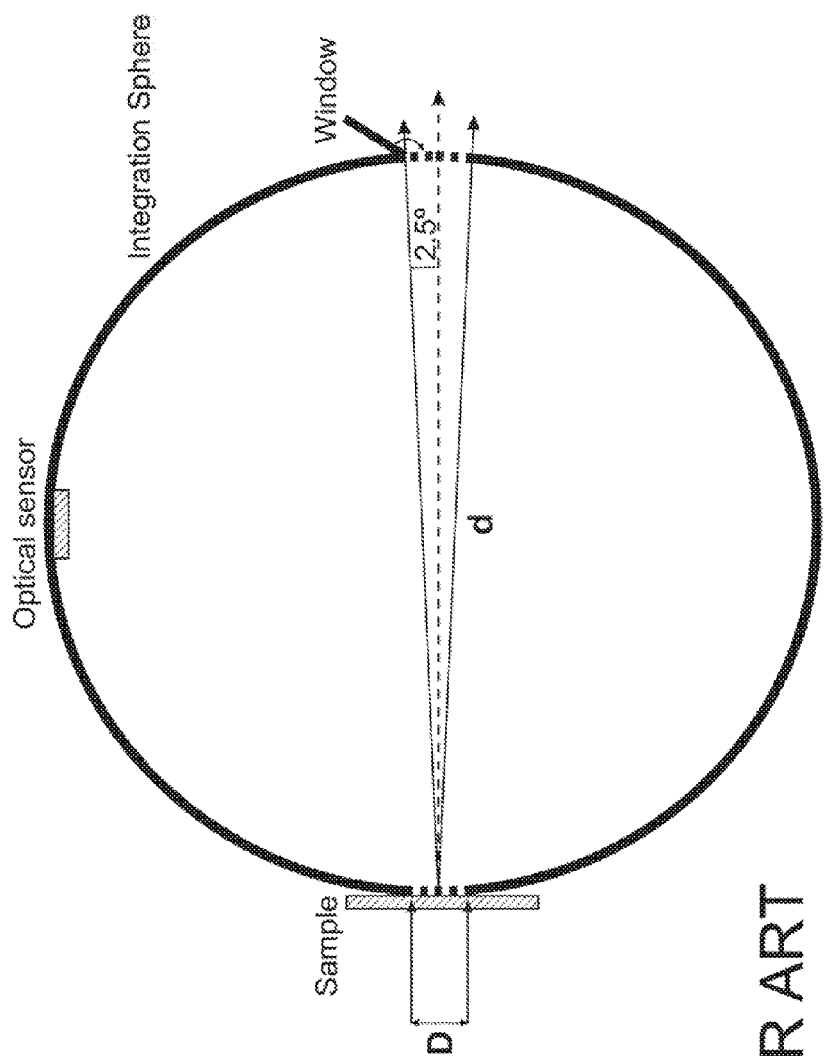
Figure 2:
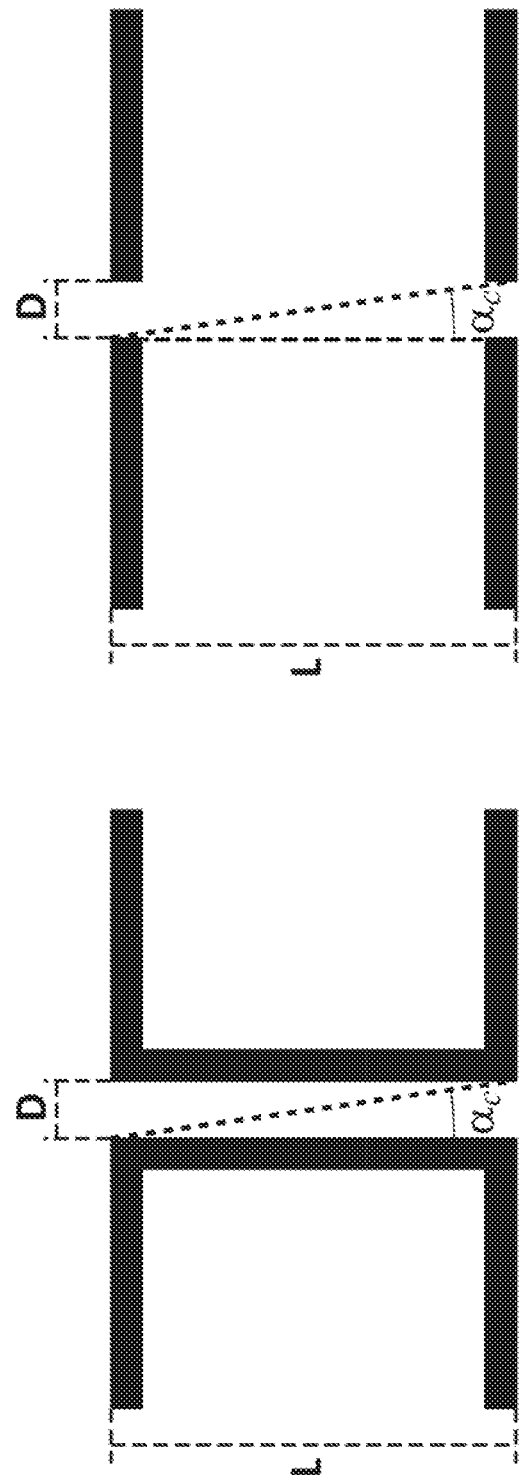
FIG. 2 shows a spatial filter, in the form of a cylinder or two apertures

In FIG. 2 (left) the cut-off $\alpha_c$ angle of the k vectors passing through a cylinder tube is defined by the diameter D and length L of the tube.

$$\alpha_c = \arctan\left(\frac{D}{L}\right) \tag{5}$$

The same cut-off $\alpha_c$ angle can be achieved with two aligned circular apertures with equal diameters and external surfaces separated at a distance L, as it is shown in FIG. 2 (right).

Figure 3:
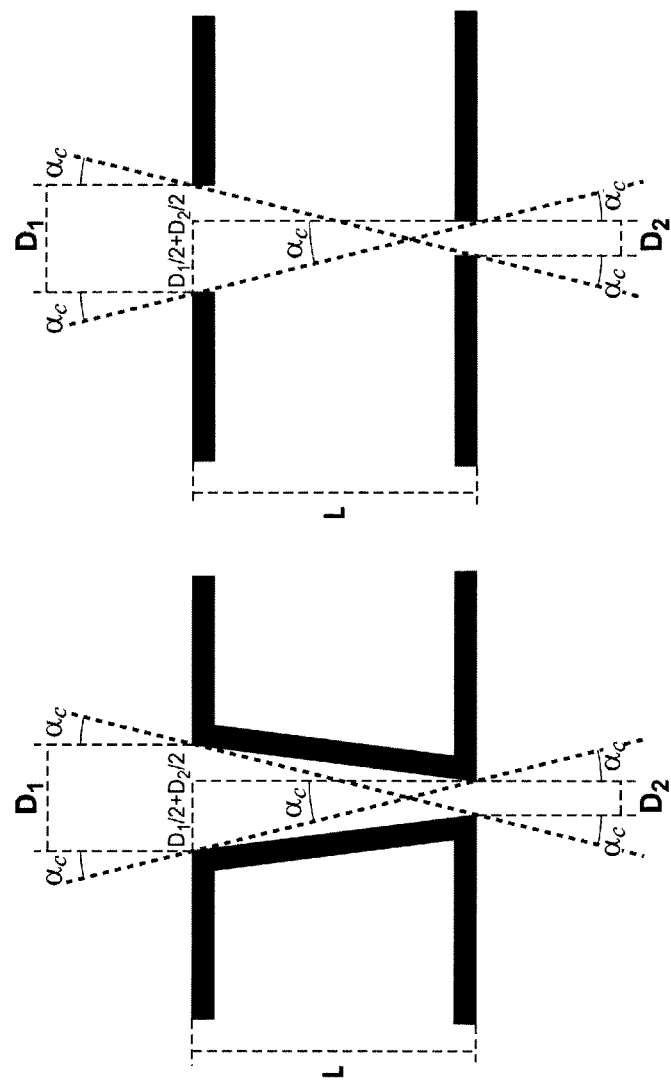
FIG. 3 is similar to FIG. 2, the filters having apertures of different diameters.

FIG. 3 (left) shows a filter consisting in a conical tube defined by its length and two different apertures in its edges and a filter consisting in two apertures separated a distance L (right). The cut-off $\alpha_c$ angle of the k vectors passing through the apertures is defined by the diameters $D_1$, $D_2$ and length L.

$$\alpha_c = \arctan\left(\frac{D_1 + D_2}{2 \cdot L}\right) \quad (5)$$

The filters could be advantageously made of a material (at least the inner walls) with high absorption over the spectrum of the light of the source. Examples of suitable materials are plastic (preferentially of black color), slate and Teflon®. When the filter presents a residual reflection, it may be preferable to use the apertures design in order to avoid possible internal reflection from the inner walls of the cylindrical tube.

The circular surface area of the spot illuminating the sample with diameter Dc is the field of view (FOV) of the spatial filter at a distance d. Only beamlets (k vectors) coming from points inside the FOV will reach the photodetector. Dc is defined as:

$$D_c = D_1 + 2 \cdot d \cdot \tan(\alpha_c) \quad (6)$$

Figure 4:
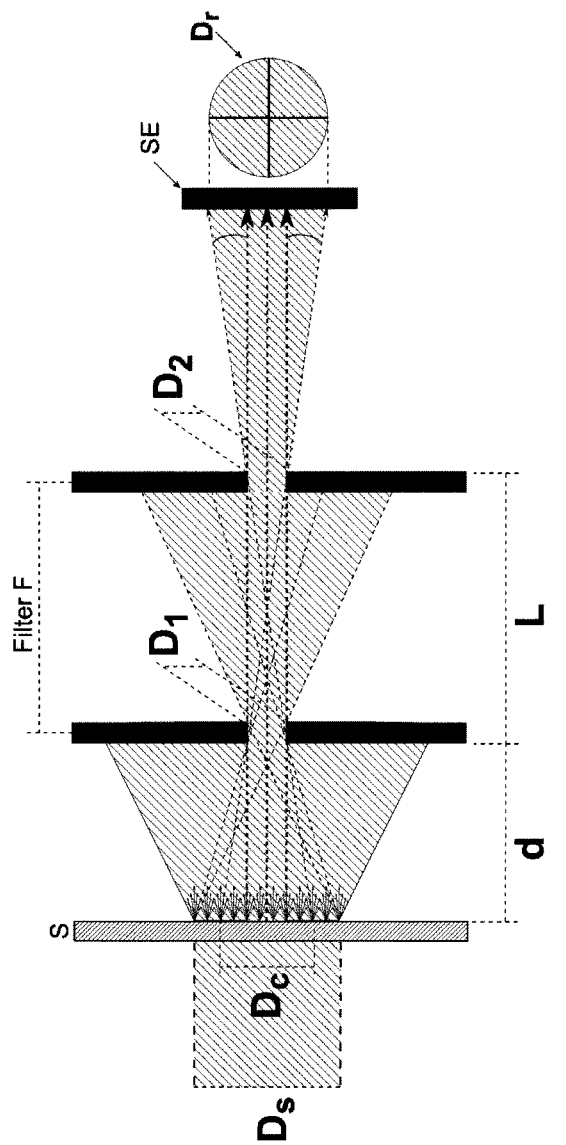
FIG. 4 shows the relationship between the diameter of the beam, the field of view and the diameter(s) and length of the filter.

As shown in FIG. 4, the circular surface area of the spot exiting the spatial filter and arriving to the sensor with diameter Dr is the back field of view of the spatial filter at a distance dr. The sensor surface must be equal or larger than the spot surface Dr in order to contain all the light power exiting the spatial filter. In case dr=0, sensor surface must be equal or larger than the second aperture. Dr is defined as:

$$D_r = D_2 + 2 \cdot d_r \cdot \tan(\alpha_c) \quad (6')$$

The embodiment of FIG. 4 shows a collimated beam, with diameter Ds, illuminating a sample and two separate apertures. A diverging beam, i.e coming from a hazy sample placed before the filter, passes through the spatial filter. The spatial filter has a particular FOV equal to Dc. That means the optical sensor after the spatial filter only "see" Dc surface of the sample. Taking this into account, it is necessary that the input collimated beam has a spot diameter Ds equal or larger than Dc. If Ds were smaller than Dc the sensor would see a non-illuminated part of the sample. The spatial filter blocks any k vector with angle higher than $\alpha_c$.

The light sensor can be placed touching the D2 aperture or at a distance. Its active area, with diameter Dr, has to be equal or larger than the area of the beam spot exiting the spatial filter in order to avoid errors in power light measurement.

Figure 5:
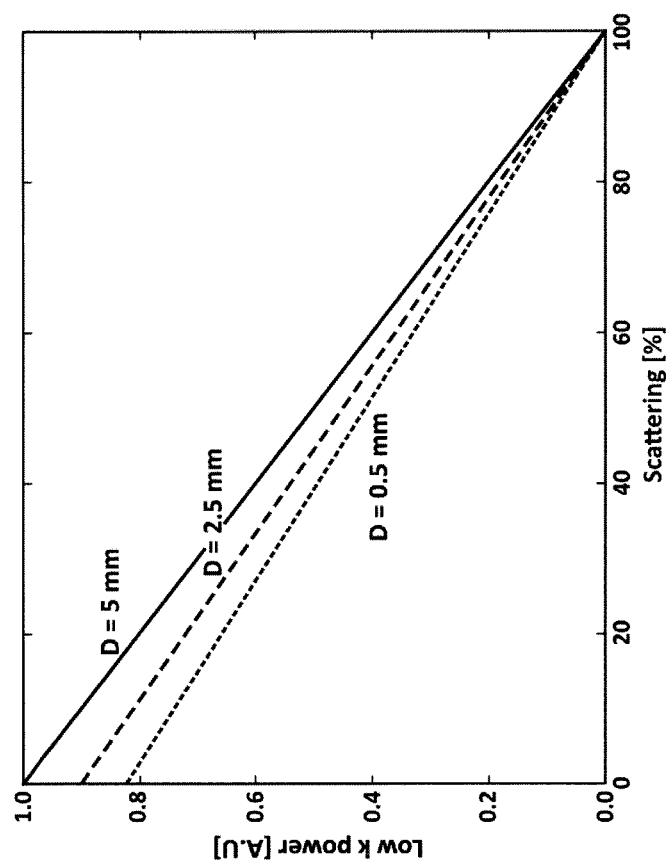
FIG. 5 is a graph of the low k power versus scattering for various apertures.

FIG. 5 shows the calculated low k power as a function of scattering for various spatial filter apertures. Scattering here is represented as scattering percentage (the percentage of scattered light power related to total light power). The slope of the curves and the nominal value for a particular scattering, increases with D. That means the invention has better accuracy measuring low k vectors using spatial filters with higher apertures. This design condition defines the effective area of the photodiode or of the image sensor, because a sensor area equal or larger than the spatial filter area is needed in order to measure the low k power without errors.

Figure 6:
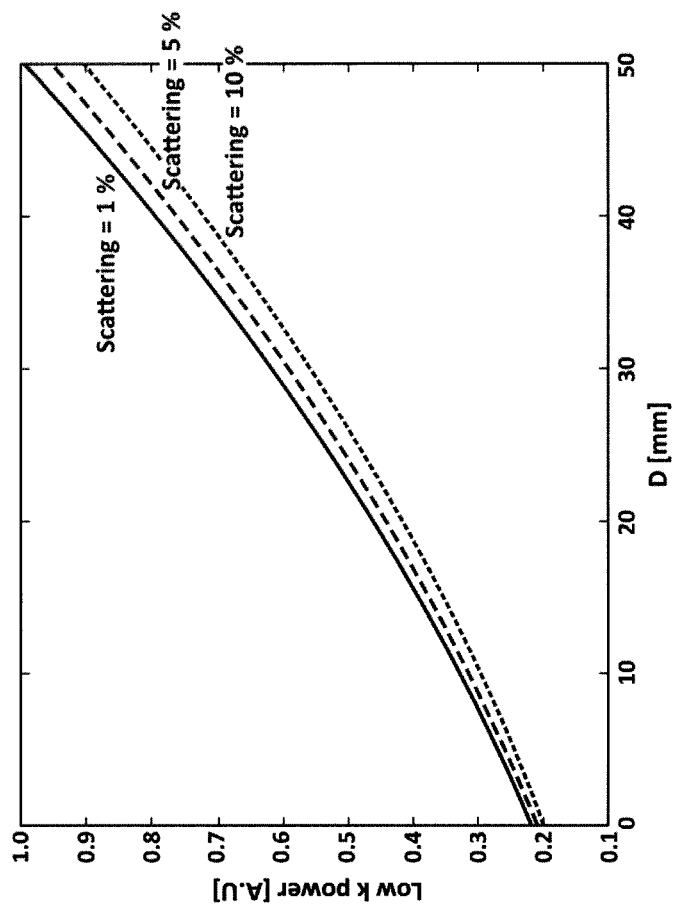
FIG. 6 is a graph of the low k power versus different apertures for three samples with different haze.

FIG. 6 shows the calculated low k power as a function of the spatial filter aperture for various samples with different scattering percentage. Low k power increases with filter diameter but the slope of the curves, and the nominal value for a particular diameter, decrease with scattering. That means for a particular D, the invention has better accuracy measuring low k vectors in samples with lower scattering.

The preferred conditions to enhance the accuracy of the invention are: a short distance between sample and spatial filter, large diameters of apertures and large area of the photodetector or light sensor.

Figure 7A:
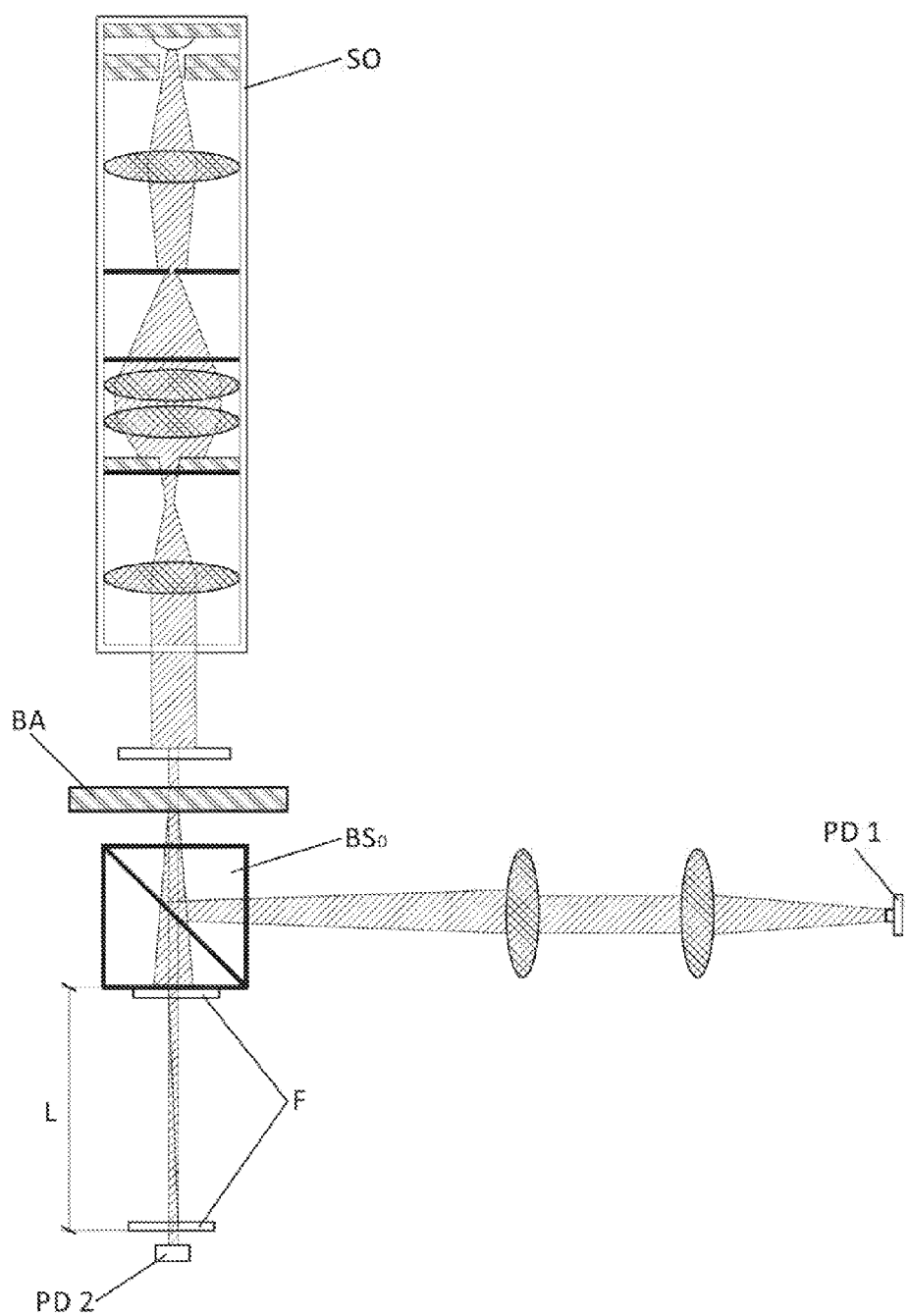
FIGS. 7a-7d show embodiments of the invention using a beam splitter to measure total k power and low k power.

In a first embodiment, total power is measured by means of a beam splitter or mirror (FIG. 7a). The scattered light is split into two beams; the low k vectors' power is measured from the first beam by means of a spatial filter F as shown in FIG. 7a, with $\alpha_c=2.5°$ (that is, in this particular example, we measure haze as in the definition given above). The total power is measured collecting the whole power of the second beam.

As one possible implementation of this embodiment, FIG. 7a shows a light source SO, preferably a white light source, such as a light emitting diode LED, with a collimation system for the light source, preferably a Köhler system, illuminating a hazy sample, a beam splitter $BS_0$, preferably with 50/50 split percentages, a lens or lenses to collect the total forward scattered power and a first photodiode to measure it, a spatial filter and a second photodiode to measure the low k power.

To achieve a collimated and homogeneous input beam a Köhler illumination followed by a collimation lens setup is used. A white light source LED illuminates the collimation system and after a 1 mm diameter aperture, the homogeneous and collimated beam impinges on the hazy sample. A 50/50 beam splitter splits it into two beams. One beam is collected by the photodiode PD1 which measures a signal proportional to the total power transmitted. The second beam goes through two aligned 1 mm apertures filters and is then measured by the photodiode PD2. This measurement is proportional to the low k vectors power. The diameters and the separation sets the filter cut-off angle at 2.5°, angle established by the haze standards EPA 180.1 and ISO 7027.

The haze value in the first preferred embodiment can be calculated:

$$V_{PD1}^S = R_1 \cdot A/100 \cdot P_T^S \quad (7)$$

$V_{PD1}^S$ is the voltage in the PD1 photodiode output, $R_1$ is its responsivity in [V/W], and A is the percentage of the light split to into the first beam.

$$V_{PD2}^S = R_2 \cdot B/100 \cdot P_{LA}^S \quad (8)$$

$V_{PD2}^S$ is the voltage in the PD2 photodiode output, $R_2$ is its responsivity in [V/W], and B is the percentage of the light split into the second beam.

A and B are factors which are known to the skilled person and depend on the beam splitter. If a 50/50 beam splitter is used, A=B.

$V_{PD1}^R$ and $V_{PD2}^R$ measures $P_T^R$ and $P_{LA}^R$, respectively, in the reference measurement without any sample.

According to the previous definitions of $$H_S = \left(1 - \frac{P_{LA}^S}{P_T^S}\right) \text{ and } H_R = \left(1 - \frac{P_{LA}^R}{P_T^R}\right),$$

the low k power can be written as a function of haze:

$$P_{LA}^S = (1 - H_S) \cdot P_T^S \quad (9)$$

Substituting in equation (8):

$$V_{PD2}^S = R_2 \cdot B/100 \cdot (1 - H_S) \cdot P_T^S \quad (10)$$

Dividing equation (10) by (7):

$$\frac{V_{PD2}^S}{V_{PD1}^S} = \left[\frac{R_2 \cdot B/100}{R_1 \cdot A/100}\right] \cdot (1 - H_S)$$

$$\frac{V_{PD2}^S}{V_{PD1}^S} = K_{cal}^{-1} \cdot (1 - H_S) \text{ where } K_{cal} = \left[\frac{R_1 \cdot A}{R_2 \cdot B}\right]$$

$K_{cal}$ is a calibration factor depending on the beam splitter and photodiodes, known by a person skilled in the art.

Therefore the haze sample $H_s$ can be calculated as $$H_S = 1 - K_{cal} \frac{V_{PD2}^S}{V_{PD1}^S} \quad (11)$$

Similarly for the measured reference voltages:

$$H_R = 1 - K_{cal} \frac{V_{PD2}^R}{V_{PD1}^R} \quad (12)$$

And the haze value becomes:

$$H[\%] = 100 * \left[\left(1 - K_{cal} \frac{V_{M2}^S}{V_{PD1}^S}\right) - \left(1 - K_{cal} \frac{V_{M2}^R}{V_{PD1}^R}\right)\right] \quad (13)$$

The procedure is as follows:
1. Calculate $K_{cal}$, depending on the beam splitter and photodiodes.
2. Measure without any sample the voltage values of $V_{PD1}^R$ and $V_{PD2}^R$.
3. Measure without a hazy sample the voltage values of $V_{PD1}^S$ and $V_{PD2}^S$.
4. Apply to the low k measurement the error correction of the equation (11) obtaining $V_{M2}^R$ and $V_{M2}^S$.
5. Calculate Equation (13) with the previous calculated and measured values.

Figure 7B:
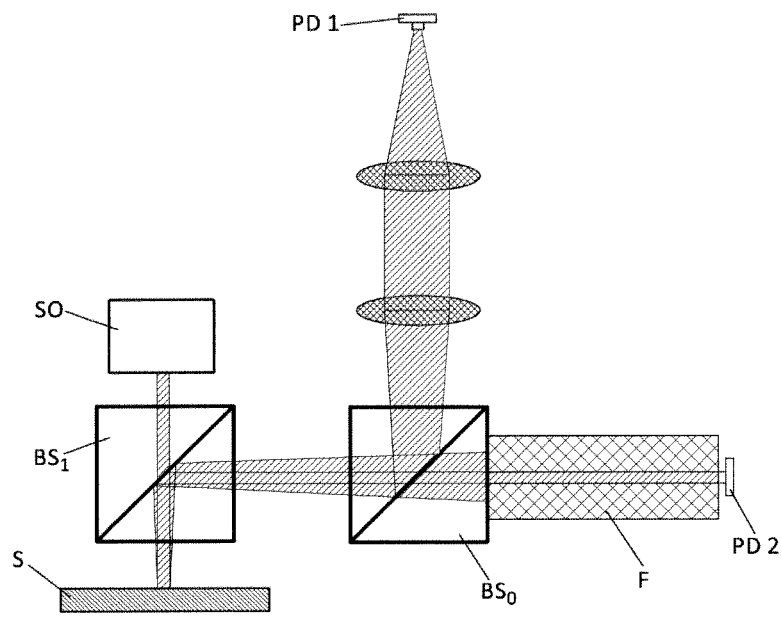

There are other possible embodiments involving the use of a beam splitter or mirror for measuring the total k power in which the measurements are done in a reflection mode. As it can be seen in FIG. 7b . . . in a reflection mode, a collimated beam illuminates perpendicularly a hazy sample and is reflected by a beam splitter $BS_1$. The reflected light is deflected by a second beam splitter $BS_0$ in order to measure the low k power and the total k power in a different direction (perpendicular or other) of the illuminating beam in the same way as in the previous embodiment. Low k power is measured from the first split beam by means of a spatial filter F and a photodiode PD2 and total k power is measured from the second split beam collecting the whole light power by means of a lens system and another photodiode PD1.

In another implementation, multiple spatial filters $F_N$ for different cut-off angles can be used.

Figure 7C:
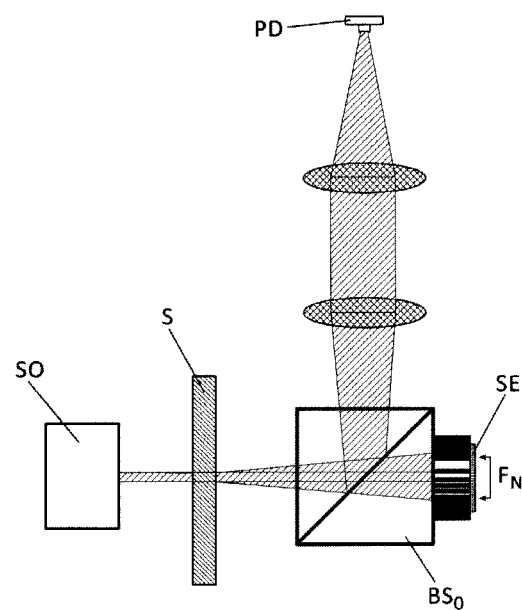

Low k power referred to different cut-off angles can be measured with different spatial filters placed inside one of the split beam exiting the beam splitter. Spatial filters can be placed preferably uniformly distributed in a plane perpendicular to the light beam direction and close, or touching the beam splitter, as it is shown in FIG. 7c.

In another implementation, multiple spatial filters, for different cut-off angles in a reflection mode can be used.

Figure 7D:
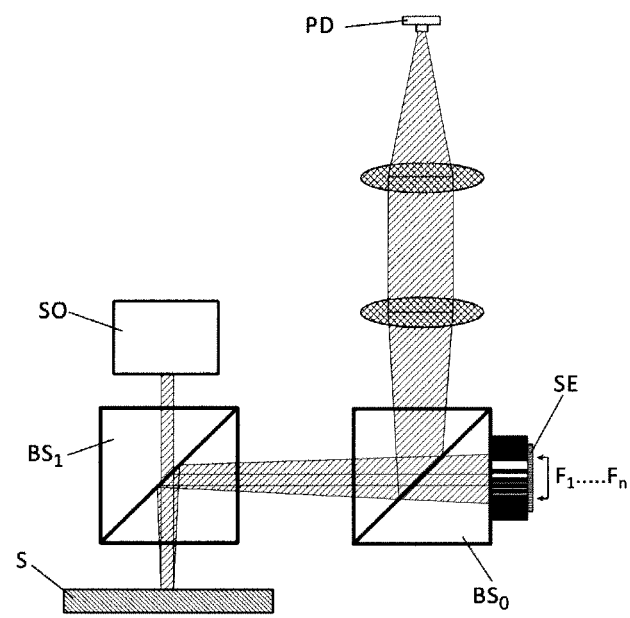

Low k power referred to different cut-off angles can be measured from one of the beams exiting the second beam splitter, as it is shown in FIG. 7d.

Figure 8A:
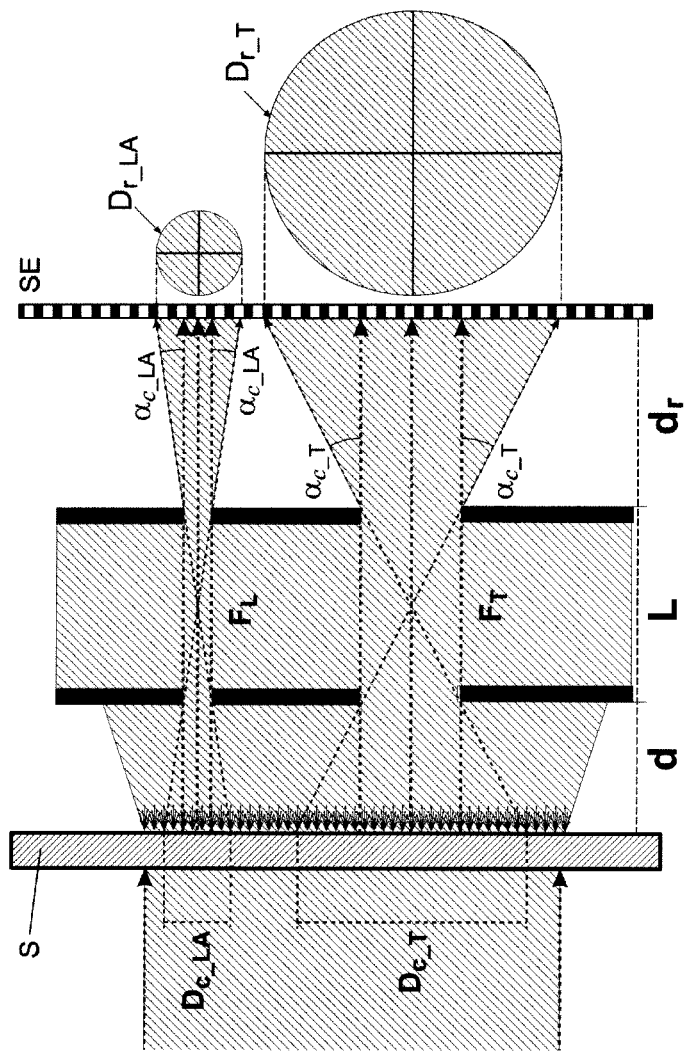
FIGS. 8a-8d show embodiments of the invention using at least two filters, one for measuring the low k power and another one for measuring the total k power.

In another embodiment, shown in FIG. 8a, the low k vector's power is measured by means of a spatial filter $F_L$ with $\alpha_c$=2.5 degree. The total power is measured by means of a second spatial filter $F_T$ with a high $\alpha_c$. To avoid errors in the total power measurement $\alpha_c$ has to be high enough that the spatial filter does not significantly cut any k-vectors. Any haze range can be measured accurately choosing adequately the ratio D/L of the spatial filter to measure the total power, as it is shown in table.

| | Measurable Haze Range [%] | | | | | | |
|---|---|---|---|---|---|---|---|
| | 0-2 | 0-10 | 0-25 | 0-50 | 0-75 | 0-99 | 0-99.99 |
| Minimum D/L of Total K Filter | 0.04 | 0.05 | 0.06 | 0.08 | 0.13 | 0.84 | 9.51 |

In this geometry both measurements, low k power and total power, can be measured with spatial filters with equal FOVs, i.e low k power is measured with a spatial filter at a distance 1 cm whose first aperture is 0.40 mm and total k power is measured with a spatial filter at a distance 1 cm whose first aperture is 0.40 mm too, only differing in the length of the spatial filter. Since FOV is depending on the first aperture and the distance, in this case, both power measurements are related with the same sample's area, and power ratio calculation for haze will be correct. But, both measurements, low k power and total power, can be measured too with spatial filters with different FOVs. That is different first apertures diameters at the same distance d, or equal first apertures diameters at different distances d, or combining different first apertures with different distances d, i.e low k power is measured with a spatial filter at a distance 1 cm whose first aperture is 0.40 mm and total k power is measured with a spatial filter at a distance 1 cm whose first aperture is 1.50 mm, The consequence is that both power measurements are referred to different size areas of the sample and for this reason the power ratio calculation for haze will be incorrect unless both measurements were adequately weighted with a rescaling factor according to:

$$FOV_{CFactor} = \frac{FOV_T}{FOV_{LA}} = \frac{[D_{c\_T} + 2 \cdot d \cdot \tan(\alpha_{c\_T})]^2}{[D_{c\_LA} + 2 \cdot d \cdot \tan(\alpha_{c\_LA})]^2}$$

Figure 8B:
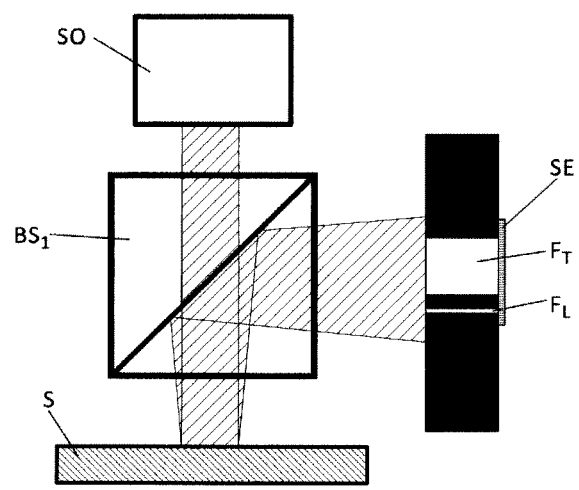

To avoid weighting errors short distance between sample and spatial filter is preferred. There are other possible embodiments involving the use of a beam splitter or mirror for measuring the total k power in which the measurements are done in a reflection mode. As it can be seen in FIG. 8b, in a reflection mode, a collimated beam illuminates perpendicularly a hazy sample and the reflected light scattering is deflected by a beam splitter in order to measure the low k power and the total power in a different direction (perpendicular or other) of the Illuminating beam. Scattered light exiting the beam splitter can be measured with the same procedure described in the previous embodiment, that is, using one or two sensors SE and by means of two filters with different D.

In another implementation, a plurality of spatial filters $F_N$ can be used for measure low k power at different cut-off angles, and the total k power.

Figure 8C:
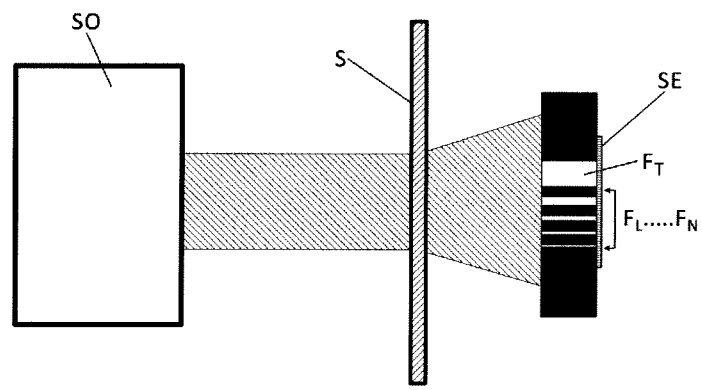

Low k power referred to different cut-off angles can be measured with different spatial filters placed inside one of the split beam exiting the beam splitter. Total power can be measured with one of the spatial filters of the array. Spatial filters can be placed preferably uniformly distributed in a plane perpendicular to the light beam direction and close, or touching the sample, as it is shown in FIG. 8c.

Figure 8D:
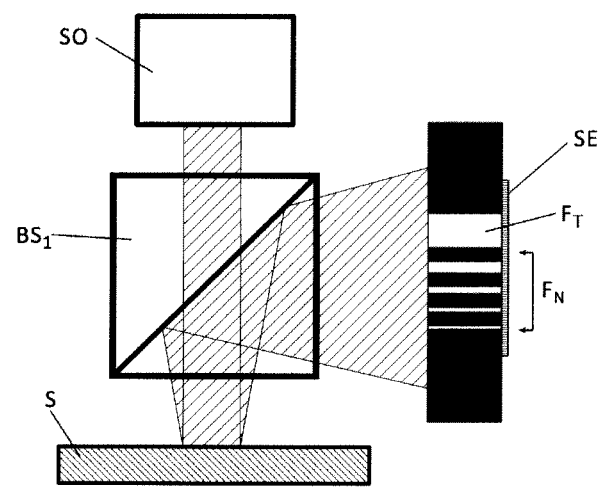

In another implementation, multiple spatial filters, for different cut-off angles in a reflection mode can be used. Low k power referred to different cut-off angles can be measured from one of the beams exiting a beam splitter used in order to measure the low k power and the total power in a different direction (perpendicular or other) of the illuminating beam as it is shown in FIG. 8d.

Since a plurality of spatial filters is used to measure low k power at different cut-off angles, these scattering power values can be represented in a scattering radiation diagram. An example of a plurality of spatial filters for measuring a scattering radiation diagram for angles between 1.25 and 9.31 degree is shown in the following table:

| | Diameter Apertures[mm] | | | | | | | | |
|---|---|---|---|---|---|---|---|---|---|
| | 1.5 | 1.3 | 1 | 0.9 | 0.8 | 0.7 | 0.6 | 0.4 | 0.2 |
| Length Tube [mm] | 9.15 | 9.15 | 9.15 | 9.15 | 9.15 | 9.15 | 9.15 | 9.15 | 9.15 |
| Cutt-off Angle Alpha [°] | 9.31 | 8.09 | 6.24 | 5.62 | 5.00 | 4.37 | 3.75 | 2.50 | 1.25 |

Since an image sensor is used to measure the light power of a plurality of spatial filters, and each group of pixels is in charge of measure the light power of each spatial filter, the shadow and diffracted image of the sample provided by each group of pixels can be processed by image processing techniques in order to obtain a microscopic resolved image, with a resolution equal to the pixel size and a field of view equal to the image sensor dimensions. Image processing techniques to recover amplitude and phase from a diffracted image are well known in holographic reconstruction and lens-free microscopy.

In this text, the term "comprises" and its derivations (such as "comprising", etc.) should not be understood in an excluding sense, that is, these terms should not be interpreted as excluding the possibility that what is described and defined may include further elements, steps, etc.

On the other hand, the invention is obviously not limited to the specific embodiment(s) described herein, but also encompasses any variations that may be considered by any person skilled in the art (for example, as regards the choice of materials, dimensions, components, configuration, etc.), within the general scope of the invention as defined in the claims.

The invention claimed is:

1. An apparatus for measuring light scattering of a sample S comprising:
   a light beam source SO generating a light beam;
   means for collimating the light beam and making the light beam impinge on the sample S in a perpendicular direction;
   at least one light sensor (PD1, SE);
   at least one spatial filter F between the sample and the at least one light sensor (PD1, SE), the at least one spatial filter F provided with two apertures wherein a scattering angle, $\alpha_c$, of a light beam passing through the filter is defined by:

$$\alpha_c = \arctan\left(\frac{D_1 + D_2}{2 \cdot L}\right)$$

wherein $D_1$ and $D_2$ are diameters of the two apertures, respectively, and L is the total length of the at least one spatial filter in the direction of the light beam;
   means for measuring total power reaching the at least one light sensor;
   and means for measuring power of the beams having a k vector lower than $\alpha_c$ after the light beam traverses the at least one spatial filter.

2. The apparatus according to claim 1 wherein the means for measuring the total power are a second light sensor PD2 and a beam splitter or dielectric mirror $BS_0$ for splitting the beam in two directions, a first direction of the two directions towards the at least one spatial filter F and the at least one light sensor PD1 and a second direction of the two directions towards a second light sensor PD2.

3. The apparatus according to claim 2 further comprising a second beam splitter or dielectric mirror between the sample S and the light beam source SO for allowing the apparatus to work in reflection mode.

4. The apparatus according to claim 3 comprising a plurality of N filters $F_N$, N being greater or equal than 2, with different apertures D.

5. The apparatus according to claim 4 wherein the at least one light sensor (PD1, SE) are photodiodes.

6. The apparatus according to claim 2 comprising a plurality of N filters $F_N$, N being greater or equal than 2, with different apertures D.

7. The apparatus according to claim 1 wherein the at least one light (PD1, SE) sensor are photodiodes.

8. The apparatus according to claim 1 wherein the means for measuring the total power are a second filter $F_T$ in parallel with the at least one spatial filter F between the sample S and the at least one light sensor (PD1, SE), the second filter $F_T$ having a greater aperture than an aperture of the at least one spatial filter F.

9. The apparatus according to claim 8 comprising a plurality N of filters $F_N$, N being equal or greater than 3, with different apertures D.

10. The apparatus according to claim 9 further comprising a beam splitter or mirror $BS_1$ for allowing the apparatus to work in reflection mode.

11. The apparatus according to claim 10 wherein the at least one light sensor (PD1, SE) are a CMOS camera or CCD camera.

12. The apparatus according to claim 11 where the light beam source SO is of any predetermined wavelength or white, tunable, or a light emitting diode.

13. The apparatus according to claim 8 further comprising a beam splitter or mirror $BS_1$ for allowing the apparatus to work in reflection mode.

14. The apparatus according to claim 1 wherein the at least one light sensor (PD1, SE) are a CMOS camera or CCD camera.

15. The apparatus according to claim 1 where the light beam source SO is of any predetermined wavelength or white, tunable, or a light emitting diode.

16. Use of the apparatus of claim 1 as a turbidimeter, hazemeter or glossmeter.

* * * * *

UNITED STATES PATENT AND TRADEMARK OFFICE
CERTIFICATE OF CORRECTION

PATENT NO. : 9,857,300 B2
APPLICATION NO. : 14/616062
DATED : January 2, 2018
INVENTOR(S) : Valerio Pruneri et al.

It is certified that error appears in the above-identified patent and that said Letters Patent is hereby corrected as shown below:

On the Title Page

Item (30), the Foreign Application Priority Data "41382043" should read -14382043.9-

In the Specification

Column 1, Line 7, the European Patent Application No. "41 382 043.9" should read -14382043.9-

Signed and Sealed this
Tenth Day of April, 2018

Andrei Iancu
*Director of the United States Patent and Trademark Office*